United States Patent
Zikria

(10) Patent No.: US 6,668,834 B1
(45) Date of Patent: Dec. 30, 2003

(54) ANTI-SNORING APPARATUS

(76) Inventor: Bashir Zikria, 196 Milbrook Cir., Norwood, NJ (US) 07640

( * ) Notice: Subject to any disclaimer, the term of this patent is extended or adjusted under 35 U.S.C. 154(b) by 0 days.

(21) Appl. No.: 08/967,562

(22) Filed: Nov. 12, 1997

Related U.S. Application Data

(63) Continuation of application No. 08/742,315, filed on Nov. 1, 1996, now abandoned.

(51) Int. Cl.[7] .................................................. A61F 5/56
(52) U.S. Cl. ...................................... 128/848; 602/902
(58) Field of Search ................................ 128/846, 848, 128/859–862; 602/902

(56) References Cited

U.S. PATENT DOCUMENTS

| | | | | |
|---|---|---|---|---|
| ,771,982 A | * | 10/1904 | Hiser | 128/848 |
| 2,528,370 A | * | 10/1950 | Johnston | 128/848 |
| 4,366,815 A | * | 1/1983 | Broomes | 128/848 |
| 4,700,697 A | * | 10/1987 | Mundell | 602/18 |
| 4,702,233 A | * | 10/1987 | Omicioli | 602/18 |
| 5,289,829 A | * | 3/1994 | Roehrig | 128/848 |

\* cited by examiner

*Primary Examiner*—Michael A. Brown
(74) *Attorney, Agent, or Firm*—Evelyn M. Sommer

(57) ABSTRACT

An apparatus for preventing a sleeping person from snoring while permitting normal, comfortable sleep, having a flexible shaped body means designed to be worn in proximity to the user's neck and beneath the user's chin. Said shaped body means is designed to restrict the user's forward cervical vertebral flexion, while permitting substantial flexibility of the neck in other directions to maximize comfort and permit normal sleep. The shaped body means has a first end and a second end restrained within proximity to a plane tangential to the rear of the user's neck by a connecting device, yet displaced from immediate proximity to the back of the neck and head whereby said first and second ends of said body means do not encroach between said user's neck and the associated bedding, thereby permitting normal repose. Said shaped body means is maintained in the appropriate orientation and proximity to the user's neck and chin by attachment straps passing around the user's neck and adjustablely attached by suitable fastening means.

9 Claims, 3 Drawing Sheets

ANTI-SNORING APPARATUS

This application is a continuation of application Ser. No. 08/742,315, filed on Nov. 1, 1996 entitled ANTI-SNORING APPARATUS, now abandoned.

BACKGROUND OF THE INVENTION

The present invention relates, in general, to neck collars and, particularly, to neck collars that reduce or eliminate snoring by maintaining the head of the user in an almost erect position so that the user's chin does not slump on the chest.

Snoring is a rough, hoarse noise produced by the vibration of air waves passing through a partially obstructed upper respiratory tract (trachea). The posterior pharynx and trachea are the main system of tubes through which air passes to and from the lungs. When the head is held erect, air passes through the trachea unimpededly. However, if the head and neck are flexed, the base of the tongue falls posteriorly and the trachea also becomes flexed which creates a point of partial obstruction. Air passing through this point of partial obstruction causes vibration which produce the unpleasant sound referred to as snoring.

The base of the tongue falls posteriorly and the pharynx-trachea frequently become flexed when a person is sleeping. Such a condition can occur when the head of the user droops and the chin rests on the chest. By elevating the chin away from the chest, the pharynx-trachea is straightened and the problem is solved. The effectiveness of the principle of elevating the chin is demonstrated by the fact that in all life threatening situations involving asphyxia, the base of the tongue must be stretched and the pharynx-trachea must be straightened as the first step before administering artificial respiration. Further support for this theory is provided by the fact that no one snores when awake, even when lying in bed; because when awake, the base of the tongue, posterior pharyngeal muscles and pharynx are not relaxed keeping them anteriorly elevated and the chin away from the chest by the pulley action of the muscles at the back of the neck. This control is relaxed during unconsciousness, the structures falling posteriorly obstructing the upper airway.

Initially it was assumed that an ordinary flat cervical collar such as that used for sprained necks might also serve as a device to keep the chin elevated. Subsequent observation demonstrated that the principle which determined the effectiveness of the flat collar in relieving the pains of a sprained neck, is diametrically opposite to that which would make an anti-snoring device useful. In the former, the intended purpose is primarily to restrict the movement of the head from side to side; since in neck sprains, downward movement of the head does not cause much pain. To be truly effective, the sprain collar must be wide enough to envelope at least the lower portion of the chin to immobilize the head. When this, however, has been attained, it is then easy for the chin to slip downwards between the edges of the enveloping collar and still rest on the chest, thereby rendering it ineffective and undependable as an anti-snoring device. In addition, such collars substantially restrict movement of the head and neck in all directions, and therefore are uncomfortable to wear and interfere with normal sleep of the wearer. Specifically, whereas it is the forward flexion of the cervical vertebrae that creates the restriction of the upper airway leading to snoring, such existing collars contrastingly restrict side and back flexion of the neck unnecessarily.

U.S. Pat. No. 4,366,815 to Broomes disclosed a flexible collar that addresses some of the problems that had existed with such collars. However, the Broomes collar is too flexible to fully restrain the head and neck in the appropriate directions.

Accordingly, the present invention has, as an object, the provision of an anti-snoring apparatus which maintains the chin markedly above the user's chest, stretching the base of the tongue and keeping the pharyngeal-tracheal angle straight with full rotational movement.

It is a further object of the invention to provide a flexible anti-snoring apparatus.

A further object of the present invention is to provide such advantageous functions while not unduly or unnecessarily restricting other normal movement of the head or neck to thereby maximize the comfort and acceptability of the apparatus and permit normal sleep.

These and other objects of the invention will become apparent upon consideration of the accompanying specification and drawings.

SUMMARY OF THE INVENTION

The present invention provides an anti-snoring device for preventing a sleeping person from making snoring sounds. The present invention provides an anti-snoring apparatus which is held securely around and under the neck and under the chin and which is simple to construct and reliable in its use.

The apparatus comprises a shaped body which when worn, lies over the anterior of a user's neck. Because the apparatus is to be worn while sleeping, the shaped body has a cross-sectional diameter that allows free side-to-side movements of the head. Despite the unrestricted lateral head motion, the device of the present invention prevents downward flexion of the head onto the user's chest. The shaped body has a first and second lateral end. Extending from each such end is a connecting cord or strap. These cords or straps attach to each other at the posterior of the user's neck by a conventional means such as, for example by a hook-and-loop system (such as Velcro®), snaps or ties. As a result, the straps maintain the position of the shaped body between the first end and second end beneath the user's chin, and the shaped body in this position maintains the user's neck in an extended position. In one embodiment of the present invention, neck straps are provided which are secured together in a way that adjusts to the diameter of the user's neck.

In another embodiment of the present invention, the apparatus is a largely flexible collar having a rigid core covered with a soft, absorbent fabric. The rigid core can be made from styrofoam and may include plastic struts.

Each attachment strap has a first proximal end attached to the cylindrical body. In a preferred embodiment, the second or distal end of each strap has a hook-and-loop fastening material attached thereto. When the straps are attached together, the anti-snoring apparatus is maintained securely and comfortably beneath the user's chin.

Snoring is caused by the passage of air through a partially obstructed trachea. This obstruction can occur during sleep when the head slumps or droops on the chest. Therefore, an effective way to eliminate snoring is by elevating the chin from the chest. This elevation must be done in a comfortable manner so as not to interrupt the sleeping person. The present apparatus allows free movement of the head and neck in all directions with the exception of downwards. Therefore, a person can comfortably sleep without disturbing others by snoring. The anti-snoring device will prevent the user from snoring and not the snorer from sleeping.

DETAILED DESCRIPTION OF THE INVENTION

Figure 1:
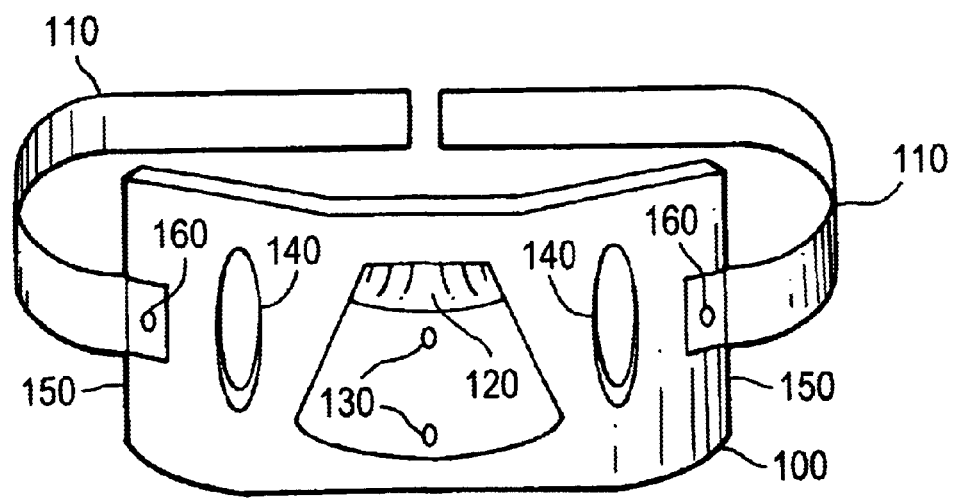
FIG. 1 is a front elevational view of an embodiment of the anti-snoring device of the present invention.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

A preferred embodiment of the present invention is shown in FIG. 1 where the anti-snoring device has a shaped body 100 with a rigid chin brace 120 desirably molded into the shaped body. At each end, 150, of the shaped body, 100, straps, or cords, 110, are attached to the shaped body. The distal end of each of the straps has a connecting means that allows the straps to be adjustablely secured together so that the straps can secure the shaped body in place about the user's neck.

In another embodiment of the present invention, shaped body 100, is a conventional soft cervical collar, approximately 1 inch thick, in which a chin brace 120 is secured in place by a conventional means, such as adhesive, sewing, rivets or clips such as plastic clips at 130. Typically, straps 110 are secured to the shaped body 100 in a similar fashion at 160.

In a further embodiment of the present invention, the shaped body 100 has a plurality of windows 140 that reduce the surface area of the neck that is covered by the shaped body without reducing the ability of the anti-snoring device of the present invention to restrain forward cervical vertebral flexion. Windows 140 can also reduce the weight of the anti-snoring device of the present invention thereby improving the user's comfort when wearing the device of the present invention.

Chin brace 120 can be made of any material that maintains the chin position and is compatible with prolonged contact with the skin. Plastic is a preferred chin brace material and acrylics such as plexiglass and other rigid plastics are particularly preferred plastics for use as chin brace material in the present invention.

It is also preferred that the chin brace is made of a size, length and width, that conforms to the user's neck. Typically, the chin brace is between about 0.125 and 0.99 inches thick and curved to rest under the user's chin at an angle of between about 100 and 145 degrees.

In a further embodiment of the present invention, the front portion of a semi-rigid cast neck brace such as that sold as the Philadelphia™ Cervical Collar, is secured to straps and the distal end of the straps have a conventional connecting means that allow the cervical collar front portion to be secured under the user's chin and restrain forward cervical vertebral flexion.

Figure 2:
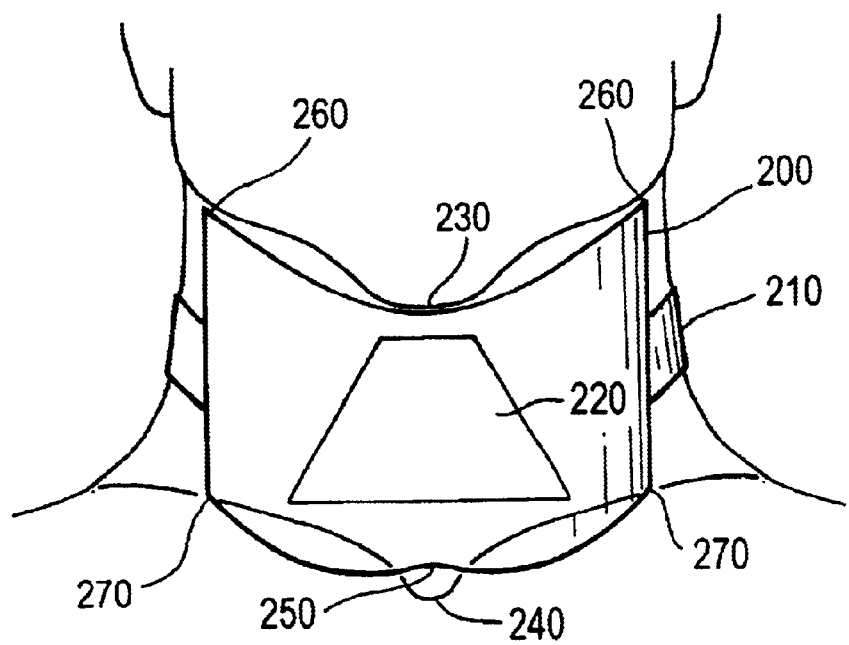
FIG. 2 is a front elevational view of a user wearing the anti-snoring device of the present invention.

FIG. 2 illustrates the use of the anti-snoring device of the present invention. The shaped body 200 is secured by straps 210 about the neck of the user with chin brace 220 restraining the user's chin from forward cervical vertebral flexion. In use, the distance from the top center of the shaped body, 230, to the bottom of the shaped body directly under position 230, should be effective to extend the tip of the chin to the manubrium to the user's fullest comfortable neck extension. Furthermore, it is preferred that the distance from the top to the bottom of the shaped body between the mid-mandible, 260, and the mid-clavicle, 270, conforms to the distance when the user's neck is in its fullest comfortable extension.

Figure 3:
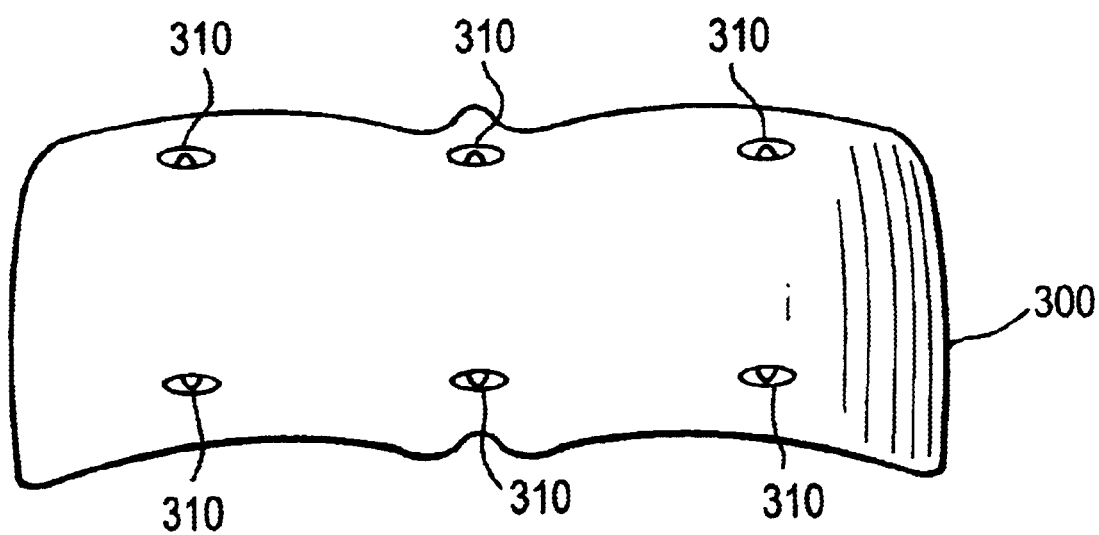
FIG. 3 is a front view of an alternative embodiment of the shaped body of the anti-snoring device of the present invention.

FIG. 3 shows an alternative embodiment of the shaped body 300 of the present invention. In this embodiment, the shaped body 300 is a modified soft cervical collar having an approximately one inch thickness and a plurality of rigid struts 310. Plastic is a preferred material for making the struts, although the struts 310 can be made of any suitable material such as a light weight metal or a wood. In a preferred version of this embodiment, there are three struts 310 rigidifying the otherwise soft cervical collar. These struts are effective to allow the collar to restrain the user's forward cervical vertebral flexion and keep the user's neck in its fullest comfortable extension. In the embodiments of the anti-snoring device of the present invention that use struts, it is preferred that the struts are secured in place by a conventional means such as adhesive, clips or rivets. Typically, the strut or struts in the center of the collar in an embodiment using struts are between about 4 and 6 inches in length and the struts in the mid-mandible area are between about 3 and 5 inches in length depending on the length of the user's neck (i.e., short, medium and long).

Figure 4:
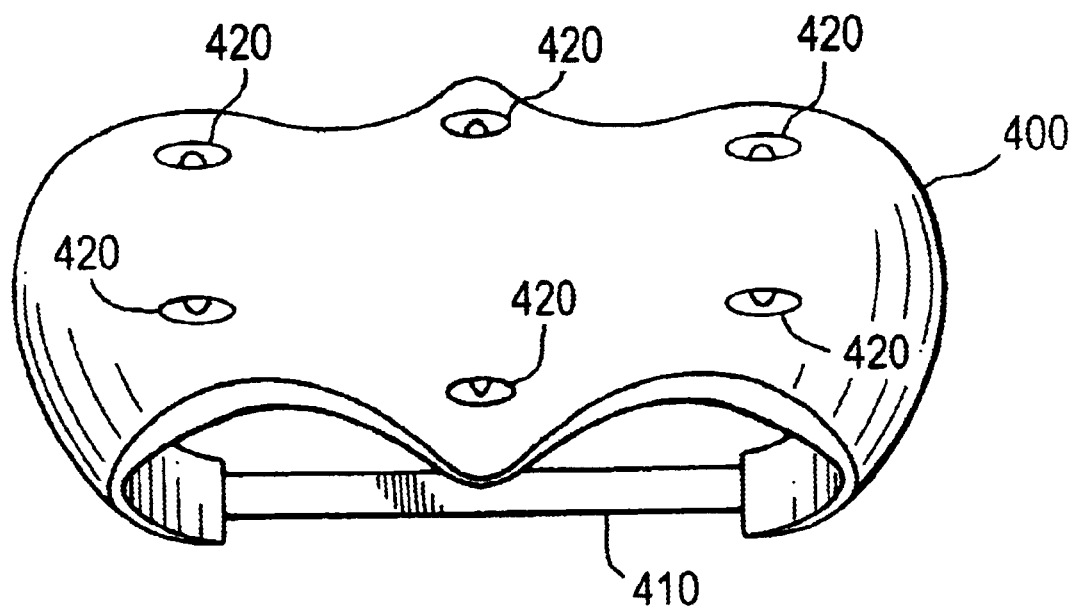
FIG. 4 is a front lower view of a further alternative embodiment of the shaped body of the anti-snoring device of the present invention showing the neck straps.

FIG. 4 shows yet another alternative embodiment of the present invention with shaped body 300 in yet another conformation. In this embodiment, shaped body 400 is again a soft cervical collar rigidified by a plurality of struts 420. Additionally, this FIG. 4 shows strap 410 that secures the collar about the user's neck.

Figure 5:
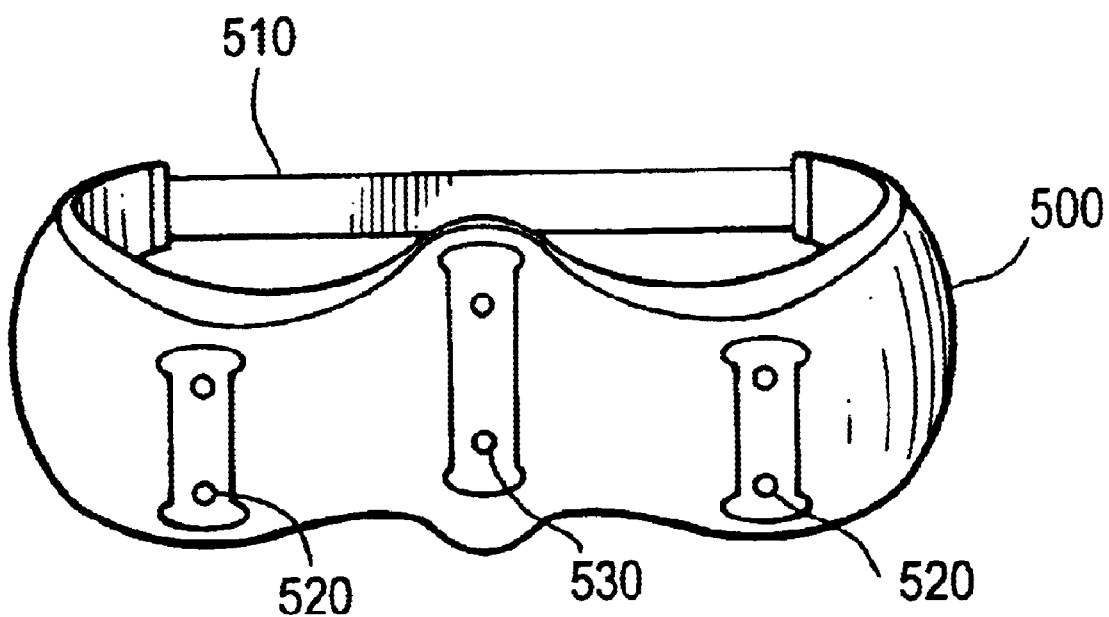
FIG. 5 is a front elevational view of still further alternative embodiment of the shaped body of the anti-snoring device of the present invention showing the neck straps.

FIG. 5 illustrates yet a further alternative embodiment of the present invention. Shaped body 500 is secured about the user's neck by straps 510 and has a plurality of struts, 520 and 530 that rigidify the otherwise soft collar so as to restrain the user's forward cervical vertebral flexion. The length of strut 530 is such that it maintains the user's neck in its fullest comfortable extension. Struts 520 are such that they ensure that the collar between the mid-mandible and the mid-clavicle conforms to distance that exists with the user's neck in its fullest comfortable extension.

In view of the above, it will be seen that the several objects of the invention are achieved and other advantageous results attained.

The inventor has found that the neck collar of the invention in addition to serving as an anti-snoring device can also function with considerable success in the treatment of other conditions.

Thus the neck collar as described herein is useful in the treatment of sleep apnea of the obstructive type. The extension of the chin and neck brought about by the collar stretches the base of the tongue and the pharyngeal muscles lifting them anteriorly resulting in the straightening of the pharyngeal-laryngeal (tracheal) angle.

Further the neck collar of the invention also aids in the prevention of wry neck or torticollis. This latter condition results from the spastic contraction of the sternocleidomastoid muscle and can be prevented by subjects prone to this condition by wearing the neck collar during sleeping periods.

Another advantage and result following from the use of the disclosed neck collar is that the collar serves to maintain the natural position of the neck and head while sleeping. In many people this hasn't heretofore been possible despite the use of different shaped pillows and pillows of varying degrees of hardness.

While the invention has been illustrated and described as embodied in an improved anti-snoring device, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What I claim is:

1. An anti-snoring device comprising:
    a) a shaped body having therein a chin brace and a plurality of windows;
    b) attached to each lateral end of said shaped body, a strap, said straps having a connecting means effective to secure said chin brace and said shaped body under the user's chin so as to restrain the wearer's neck in a position that is extended substantially as much as possible without discomforting said wearer and without substantially restricting the lateral motion of the wearer's head.

2. The anti-snoring device of claim 1 in which said chin brace is shaped so as to support said wearer's chin at an angle between 100 and 145 degrees.

3. An anti-snoring device comprising:
    a) a shaped body having therein a plurality of struts;
    b) attached to each lateral end said shaped body, a strap, said straps having connecting means effective to secure said body under the wearer's chin so as to restrain the wearer's neck in a position that is extended substantially as much as possible without discomforting said wearer.

4. The anti-snoring device of claim 3 further having a plurality of windows.

5. The anti-snoring device of claim 4 in which said windows are effective to reduce the surface area of the wearer's neck covered by said shaped body.

6. The anti-snoring device of claim 4 in which said windows reduce the surface area of the wearer's neck covered by said shaped body about 10%.

7. The anti-snoring device of claim 3 in which said struts are made of plastic.

8. The anti-snoring device of claim 7 in which said shaped body comprises a soft, absorbent fabric.

9. The anti-snoring device of claim 3 in which said struts are at least 3 inches in length.

* * * * *